United States Patent [19]

Granier

[11] Patent Number: 4,781,588
[45] Date of Patent: Nov. 1, 1988

[54] COUNTER-ANGLE HEAD FOR ENDODONTIC INSTRUMENT

[76] Inventor: Daniel Granier, quartier Petite Ile, 30150 Roquemaure, France

[21] Appl. No.: 939,405

[22] Filed: Dec. 8, 1986

[30] Foreign Application Priority Data

Dec. 18, 1985 [FR] France ................. 85 18904

[51] Int. Cl.$^4$ ............................................. A61C 1/07
[52] U.S. Cl. ..................................... 433/123; 433/122
[58] Field of Search ............... 433/118, 120, 122, 123, 433/124, 130, 105

[56] References Cited

U.S. PATENT DOCUMENTS

| 1,631,444 | 6/1927 | Warren | 433/75 |
| 2,010,210 | 8/1935 | Witt | 433/128 |
| 2,873,527 | 2/1959 | Flatland | 433/128 |
| 4,371,341 | 2/1983 | Nakanishi | 433/118 |

FOREIGN PATENT DOCUMENTS

| 0064871 | 11/1982 | European Pat. Off. |
| 0161196 | 11/1985 | European Pat. Off. |
| 0291667 | 6/1953 | Switzerland | 433/122 |
| 0295550 | 8/1928 | United Kingdom |
| 0761910 | 11/1956 | United Kingdom |
| 2011305 | 7/1979 | United Kingdom |

Primary Examiner—John J. Wilson
Assistant Examiner—Adriene J. Lepiane
Attorney, Agent, or Firm—Young & Thompson

[57] ABSTRACT

A counter-angle head for endodontic instruments comprises a body (1) in which is slidably mounted a cylindrical slide (3) clamp holder (4) tool (5) assembly. The slide is provided with at least one peripheral slot (6) in which is engaged a bearing (8) carried eccentrically by a shaft (7) rotatably mounted in a cylindrical housing (9A) of a radial extension (9) of the body (1).

The head is notable particularly in that the slide may be disengaged by retracting the bearing (8).

9 Claims, 2 Drawing Sheets

COUNTER-ANGLE HEAD FOR ENDODONTIC INSTRUMENT

BACKGROUND OF THE INVENTION

1. Field of the Invention

The present invention relates to apparatus used in endodontia and has for an object a counter-angle head for carrying a drilling or filing tool or the like.

2. Description of the Prior Art

In the preparatory stages of conditioning the dental canals prior to filling them by medicinal means, the skilled artisan proceeds first to drilling operations. For effecting such operations, there have previously been proposed various instruments comprising particularly a counter-angle head equipped with a tool-carrying clamp and means for communicating to the tool-carrying clamp and thus the tool that it carries a back and forth motion beginning with a continuous, motor movement.

Counter-angle heads of the prior art comprise a cylindrical body provided with an axial bore in which is slidably mounted the slide of the tool-carrying clamp and also comprise a tubular body in which is mounted a rotary shaft terminating in an eccentric portion that cooperates in driving with the slide of the clamp. This eccentric portion is generally constituted by an element that extends toward the slide of the clamp parallel to the longitudinal axis of the rotary shaft and which is engaged in a notch provided in the slide of the clamp.

British Pat. No. 295,550 reaches an instrument of the type described above. According to this patent, the element is engaged in a cylindrical notch of the slide and the clamp is driven, relative to its longitudinal axis, into combined reciprocating movements, namely:

a reciprocating movement of translation the length of the axis, and a reciprocating movement of rotation about the axis.

European Pat. No. 065,871 also teaches an instrument of the type described above, of which the eccentric element is engaged in a notch constituted by a groove extending parallel to the longitudinal axis of the slide. Consequently, the slide, the clamp and the tool are driven in a reciprocating rotary movement with respect to the longitudinal axis of the slide.

EP Pat. No. 0,161,196 also reaches an instrument, the eccentric member of which is engaged in a notch constituted by a groove of the slide effected along a plane perpendicular to the longitudinal axis such that the clamp and the tool are driven simultaneously in a reciprocating motion of axial translation.

The clamp of each of these instruments can be driven in only a single type of movement, which limits the applications of these instruments, whereas the usefulness of all three types of movement in the course of a single operation has been demonstrated. Moreover, the prior art instruments are not equipped with means permitting the automatic interruption of the movement of the tool when the forces applied to this latter are too great.

OBJECTS OF THE INVENTION

The present invention has for an object to overcome the previously-described disadvantages by providing a new counter-angle head with which the tool may be driven as desired by the user, in a reciprocating axial translatory motion, a rotary, oscillatory motion, and a motion resulting from the combination of these two previous motions.

Another object of the invention is to provide a counter-angle head provided with means permitting interruption of the movement of the tool if the forces exerted on this latter become too great.

SUMMARY OF THE INVENTION

To this end, the counter-angle head according to the invention, for endodontic instruments, comprises a body in which is provided an exteriorly opening bore, in which bore is slidably mounted a cylindrically shaped, clamp-carrying slide which is provided with at least one peripheral recess or notch in which is engaged a bearing carried eccentrically at the end of a shaft rotatably mounted in a cylindrical housing radial to the bore and opening into this latter. Exteriorly of the housing, the other end of the shaft carries a series of prongs which meshingly cooperate with a known motor means. The head such as described above is characterized essentially in that it is provided with a means for disengagement of the slide by retraction of the bearing.

According to another characteristic of the invention, the slide is provided with several recesses or notches distributed regularly over the periphery of the slide, which are each selectively required to come into facing relation with the bearing by rotation of the slide, and to receive the said bearing. According to yet another characteristic of the counter-angle head, the axial retractive movement of the bearing is effected against the pushing action of an elastic element calibrated such that the bearing and the corresponding notch may be spaced apart from one another when the axial force exerted by the slide on the bearing exceeds a predetermined value.

BRIEF DESCRIPTION OF THE DRAWINGS

Other advantages and characteristics of the invention will appear from a reading of the description of a preferred embodiment given by way of non-limiting example and with reference to the accompanying drawings, in which.

DETAILED DESCRIPTION OF THE INVENTION

Figure 1:
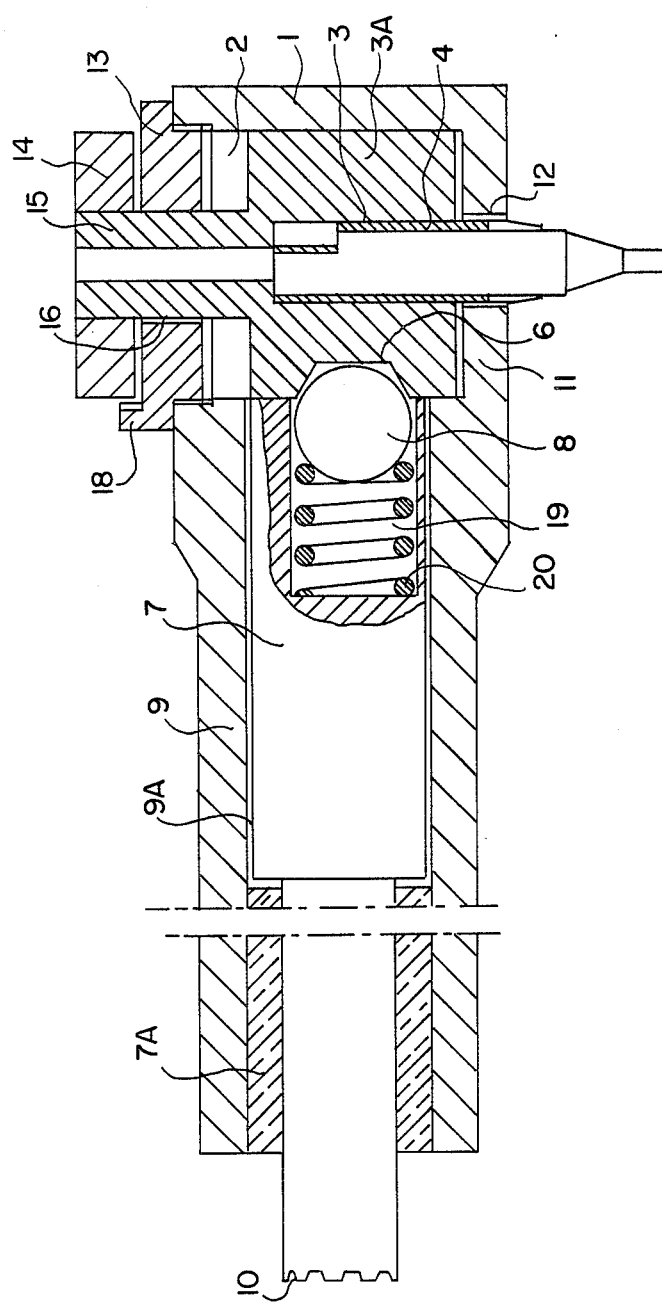
FIG. 1 is a view in longitudinal section of the head according to the invention.
Figure 2:
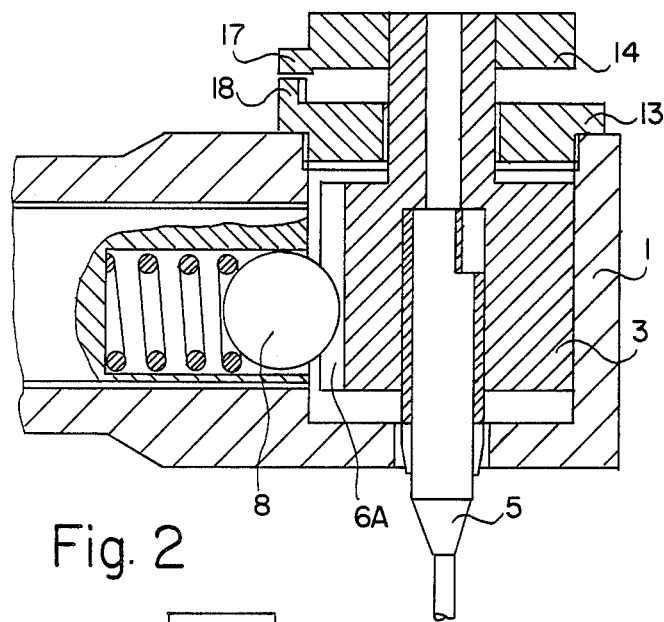
FIG. 2 is a sectional view illustrating the role of the axial abutment members.
Figure 4:
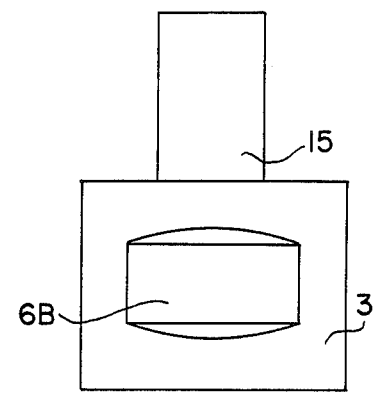
FIGS. 3, 4 and 5 are plan views of the slide each showing one of the notches.
Figure 5:
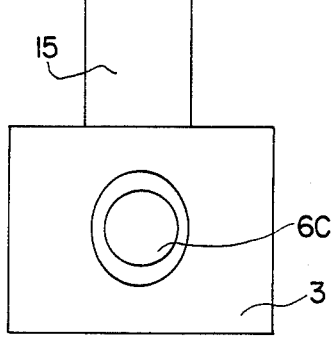
Figure 3:
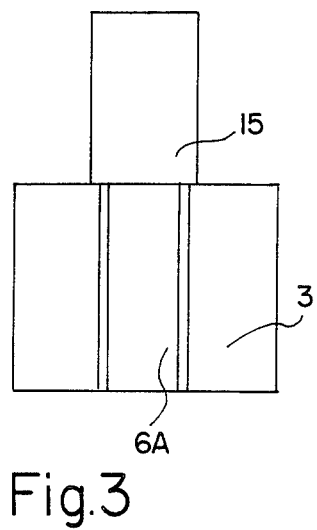
Figure 6:
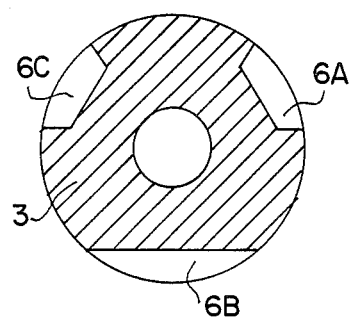
FIG. 6 is a transverse section of the slide.

As shown, the counter-angle head according to the invention for endodontic instruments, comprises a head 1 in which is provided an axial bore opening exteriorly, in which bore is slidably mounted a cylindrically-shaped slide 3 equipped with a clamp 4 which receives an endodontic tool 5. The slide 3 comprises a peripheral recess or notch 6 that enables it to be engaged by a rotary shaft 7 by engagement in the notch of a bearing 8 mounted eccentrically at the end of the shaft 7.

This shaft 7 is rotatably mounted in a cylindrical housing 9A opening radially into the bore 2 and disposed in a cylindrical extension 9 of the body 1. This extension 9 extends radially from the body 1. A sleeve 7A for guiding the shaft 7 in rotation, is disposed in the cylindrical housing 9A of the extension 9. The sleeve is of the autolubricating type and is preferably constituted of phosphorous bronze.

Exteriorly of the housing 9A, the other extremity of the shaft receives a series of prongs 10 intended to cooperate in connection with the moving mesh of a motor means, known in itself.

According to the preferred embodiment, the body 1 comprises a base 11 which extends perpendicularly to the axis of the bore. This base is pierced from one side to the other, coaxially to the bore, by a cylindrical opening 12 which constitutes a passage for the clamp 4 which is fixed by its body in a cylindrical opening 3A effected in the slide 3 along the axis of this latter.

The bore 2 is closed by a cover 13. This cover is provided at its periphery with a screw threading for cooperating in fixation with a screw threading effected in the mouth of the bore 2. The distance between the base 11 and the cover 13 is greater than the height of the slide such that the said slide may be displaced axially in the bore 2.

Via the series of prongs 10, the motor means communicates to the shaft 7 a continuous rotary movement. This rotary movement is translated by the bearing and notch system into at least one reciprocating movement which is imparted to the slide 3 with the clamp 4 and the tool 5.

According to the invention, the counter-angle head is equipped with a means for disengaging the slide by axial retraction of the bearing. Also, thanks to this means, the bearing may be disengaged from the notch of the slide and this latter may be freely manipulated.

According to another characteristic, the slide is equipped with three differently shaped notches 6A, 6B, 6C distributed regularly over its periphery, each intended to cooperate with the bearing so as to constitute with this latter a system for translating the circular movement. It will be understood that if the need arises, the slide could be equipped with one or two notches, or could receive four or more.

So as selectively to introduce each one of the notches into facing relation with the bearing, this positioning being effected by rotation of the slide, the said slide is equipped with an operating knob 14. This operating knob 14 is fixed exteriorly of the body 1 on an axial extension 15 of the slide. This axial extension, of lesser diameter than that of the slide, is engaged in an axial opening 16 of the cover 13 and passes through it from one side to the other. The operating knob 14 is fixed to this axial extension by a screw and is maintained spaced from the cover 1. Advantageously, the operating knob comprises reference marks which permit calibrating the position of the notches. The first notch 6A is constituted by a recess effected along a generatrix of the cylindrical surface of the slide. The first system constituted by the bearing and this first notch translates the continuous circular motion of the shaft 7 into an oscillating rotary motion which is communicated to the slide with the clamp and the tool, this movement being effected about the axis of the slide.

When the slide, clamp and tool assembly is driven in the first type of motion, it is advantageous to limit its axial displacement. To this end, there is provided a first abutment member fixed to the slide, clamp and operating knob assembly and a second abutment member fixed with respect to the body 1. These two abutment members, when the slide, clamp and knob assembly is driven in the first type of motion, cooperate in bearing and sliding with each other and limit the axial movement of the said assembly.

According to a preferred embodiment, the first abutment member is integral with the operating knob 14 and is constituted by a boss 17 extending toward the body 1 or the cover 13. The second abutment member is constituted by a projection 18 disposed on the cover 13.

When the first notch cooperates in coupling with the bearing, the boss of the control knob is positioned facing the projection 18 and cooperates in contact with this latter. This annular-shaped projection is developed along a circular arc centered at the longitudinal axis of the bore 2. The extent of this circular arc is equal to that of the circular arc described by a point on the slide in the course of the oscillating rotary motion. When the boss 17 is disposed in contact with the projection 18, a play of several tenths of a millimeter is established between the slide 3 and the cover 13. The axial displacement of the slide is therefore limited in this case to that value. The boss 17 cooperates with the projection 18, so as to limit the axial translatory motion of the slide, only in the scope of this first type of motion. This oscillating rotary motion is used to penetrate and enlarge the upper ⅔ of the dental canal.

The second notch 6B is constituted by a groove which is developed perpendicular to the generatrices of the cylindrical surface of the slide. This second groove, when engaged with the bearing, constitutes with this latter a second system for translation of motion. This second system translates the rotary motion of the shaft 7 into a reciprocating motion of axial translation and imparts this latter movement to the assembly of the slide 3, clamp 4 and tool 5.

This second movement permits the introduction of a catheter into, and the shaping of the apical ⅓ of the canal. It also permits the endodontic tool to pass over whatever curvatures may exist in the canals, and to correct certain anatomical irregularities.

The third notch 6C is constituted by a blind opening radial to the slide 3. This opening is preferably frustoconical. When this third notch cooperates in connection with the bearing 8, the system of translation thus constituted imparts to the bearing 3, clamp 4 and tool 5 assembly, simultaneously an oscillating rotary movement and a reciprocating axial translatory movement. This movement, with irrigation and at great speed, permits shaping, cleaning and canal wall finishing through the opening of the dentinal tubules. This latter action precedes the medicinal filling operation of the canal.

It is also possible to effect thermo-mechanical condensation of the endodontic medicinal substances by selection of the second movement. It is also possible by isolated selection of the third movement to effect the parietal finishing of the canals prior to closing them after manual drilling.

As previously stated, the counter-angle head is provided with disengagement means for the slide by retraction or extension of the bearing. Preferably, the retraction movement of the bearing is a movement of translation which is effected parallel to the longitudinal axis of the shaft 7 but it will be understood that this movement could be effected obliquely to this axis.

According to the preferred embodiment, the means permitting the disengagement of the slide is constituted by an opening 19, effected in the end of the shaft 7, in which is slidably mounted the bearing 8. According to a first embodiment, the axis of this opening is parallel to the axis of the shaft 7. According to another embodiment, the axis of this opening is oblique with respect to the axis of the shaft 7, such that the bearing may, under the effect of the axial component of the centrifugal force, be pressed into the corresponding notch.

An elastic compression member 20 is mounted in the opening 19. The movement of retraction of the bearing is effected against the pushing force exerted by the elastic member 20 and results in the mechanical action of the wall of the corresponding slot against the bearing.

To displace the bearing, the mechanical action must not be purely radial to this latter but must have an axial component of sufficient intensity to overcome, on the one hand, friction, and on the other hand, the action of the elastic member 20. To this end, each slot is flared exteriorly of the slide such that the surfaces intended to cooperate in contact with the bearing are oblique relative to the axis of displacement of this latter, which permits creating the axial component. Also, to create this axial component, the surfaces of the bearing cooperating with the slot are oblique relative to the axis of the bearing.

According to the preferred embodiment, the contour of the transverse section of each slot is a trapezoid, but it could also be a circular arc. According to this embodiment, the bearing is constituted by a ball.

Preferably, the elastic member is a helical spring. Advantageously, this spring is calibrated such that the disengagement of the slide intervenes only when the intensity of the forces exerted on this latter and/or on the tool exceeds a predetermined value and induces an axial component favoring disengagement of the endodontic tool.

The slot of the slide, and the bearing are disengaged from one another when a sufficient couple is exerted on the operating knob 14 for selecting one of the three movements in which the tool may be driven. Coupling of the selected notch and the bearing is effected automatically under the force of the thrust of the elastic member, as soon as the said notch and the said bearing are facing one another.

It will be readily understood that, thanks to the technical characteristics described above, the counter-angle head is more useful and reliable.

I claim:

1. In a counter-angle head for endodontic instruments, comprising a body having a bore, a cover covering said bore, a cylindrical slide slidably mounted in said bore, said slide having a clamp carrier adapted to clamp a tool therein, said slide further comprising at least one peripheral slot, said body having a cylindrical housing extending radially from said bore and communicating therewith, said cylindrical housing having rotatably mounted therein a shaft carrying a bearing mounted eccentrically relative to said shaft, said bearing adapted to enter into said at least one peripheral slot; the improvement comprising means for retracting said bearing to disengage said bearing from each said at least one peripheral slot.

2. Counter-angle head according to claim 1, wherein said at least one peripheral slot is a plurality of said slots regularly distributed over the periphery of said slide, each said slot having a different contour adapted to coact with said bearing to impart to said slide, upon rotation of said shaft, a respectively different motion.

3. Counter-angle head according to claim 2, wherein said plurality of peripheral slots comprises a first slot extending parallel to the axis of said slide, a second slot extending perpendicular to the axis of said slide and a third blind opening that is circular and extends radially of said slide.

4. Counter-angle head according to claim 1, wherein said retracting means comprises a blind opening formed at one end of said shaft, in which said blind opening said bearing is slidable mounted.

5. Counter-angle head according to claim 4, wherein said blind opening has an axis parallel to the axis of said shaft.

6. Counter-angle head according to claim 4, said retracting means further comprising resilient means disposed in said blind opening and urging said bearing into engagement with said at least one peripheral slot.

7. Counter-angle head according to claim 6, each said at least one peripheral slot having a contour coacting with said bearing such that rotation of said slide within said bore beyond a predetermined angular range is effective to slide said bearing in said blind opening radially outwardly from said bore against the action of said resilient means, thereby to disengage said bearing from said at least one peripheral slot.

8. Counter-angle head according to claim 7, wherein said first and third slots have a trapezoidal transverse section.

9. Counter-angle head according to claim 1, wherein said bearing is a ball

* * * * *